(12) United States Patent
Laidevant et al.

(10) Patent No.: US 7,675,044 B2
(45) Date of Patent: Mar. 9, 2010

(54) METHOD AND DEVICE FOR 3D RECONSTRUCTION OF THE DISTRIBUTION OF FLUORESCENT ELEMENTS

(75) Inventors: Aurélie Laidevant, Rumilly (FR);
Anabela Da Silva, Marseilles (FR);
Jean-Marc Dinten, Lyons (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/888,579

(22) Filed: Jul. 31, 2007

(65) Prior Publication Data
US 2008/0067420 A1 Mar. 20, 2008

(30) Foreign Application Priority Data
Aug. 2, 2006 (FR) .................................. 06 07065

(51) Int. Cl.
*G01N 21/64* (2006.01)
(52) U.S. Cl. ................................ 250/458.1; 250/459.1
(58) Field of Classification Search .............. 250/458.1, 250/459.1
See application file for complete search history.

(56) References Cited

U.S. PATENT DOCUMENTS 6,304,771 B1 10/2001 Yodh et al. .................. 600/476

2002/0072677 A1 6/2002 Sevick-Muraca et al. .... 600/473

FOREIGN PATENT DOCUMENTS

| GB | 2 231 958 A | 11/1990 |
| WO | WO 96/26431 | 8/1996 |
| WO | WO 2005/043138 A1 | 5/2005 |
| WO | WO 2006/032151 A1 | 3/2006 |

OTHER PUBLICATIONS

Laidevant et al., "Experimental study of time-resolved measurements on turbid media: determination of optical properties and fluorescent inclusions characterization." European Conference on Biomedical Optics, Jun. 12-16, 2005, Munich, Germany.*
Laidevant et al., "Experimental study of time-resolved measurements on turbid media: determination of optical properties and fluorescent inclusions characterization." Proc. of SPIE-OSA Biomedical Optics, vol. 5859, 58591F (Oct. 7, 2005) (nine pages).*
Dinten et al., "Performance of different reflectance and diffuse optical imaging tomographic approaches in fluorescence molecular imaging of small animals." Proc. SPIE, vol. 6142, 614215 (Mar. 2, 2006) (10 pages).*

(Continued)

*Primary Examiner*—Constantine Hannaher
(74) *Attorney, Agent, or Firm*—Nixon Peabody LLP

(57) ABSTRACT

A device and method for processing fluorescence signals emitted after excitation by radiation coming from a radiation source, by at least one fluorophore with a lifetime $\tau$ in a surrounding medium, which signals are detected by detection means, and which method includes the calculation, on the basis of detected fluorescence signals, of values of a variable, independent of $\tau$, of the position or the distribution of fluorophore in said medium.

26 Claims, 6 Drawing Sheets

OTHER PUBLICATIONS

French Preliminary Search Report, dated Mar. 19, 2007, French Application No. 0607065.

F. Gao, W. Liu, H. Zhao, Y. Tanikawa, A. Marjono, and Y. Yamada, "Time-Domain Fluorescence Molecular Tomography Based on Generalized Pulse Spectrum Technique," in *Biomedical Optics*, Technical Digest (CD) (Optical Society of America, Mar. 19, 2006), paper TuI15.

Kumar, A.T.N. et al., "Fluorescence-lifetime-based tomography for turbid media", Opt. Lett. 30 (24), 3347-3349 (2005).

Lagarias, J.C. et al., "Convergence Properties of the Nelder-Mead Simplex Method in Low Dimensions", SIAM Journal on Optimization, vol. 9 (1), p. 112-147 (1998).

Lam, S. et al., "Time Domain Fluorescent Diffuse Optical Tomography: Analytical Expressions", Optics Express, vol. 13, No. 7, p. 2263-2275 (2005).

Arridge, S.R. et al., "The Theoretical Basis for the Determination of Optical Pathlengths in Tissue: Temporal And Frequency Ananlysis", Physics of Medical Biology, vol. 37, No. 7, pp. 1531-1560, 1992.

Bremer, Christoph et al., "Optical-Based Molecular Imaging: Contrast Agents and Potential Medical Applications", European Radiology, vol. 13, No. 2, pp. 231-243, Feb. 2003.

Cubeddu, R. et al., "Imaging of Optical Inhomogeneities in Highly Diffusive Media: Discrimination Between Scattering and Absorption Contributions", Applied Physics Letters, vol. 69, Issue 27, pp. 4162-4164, Dec. 30, 1996.

Gandjbakhche, Amir H. et al., "Effects of Multiple-Passage Probabilities on Fluorescent Signals From Biological Media", Applied Optics, Vol. 36, No. 19, pp. 4613-4619, Jul. 1, 1997.

Godavarty, Anuradha et al., "Three-Dimensional Fluorescence Lifetime Tomography", Medical Physics, vol. 32, No. 4, pp. 992-1000, Apr. 2005.

Hall, David et al., "Simple Time-Domain Optical Method for Estimating the Depth and Concentration of a Flourescent Inclusion in a Turbid Medium", Optics Letters, vol. 29, No. 19, pp. 2258-2260, Oct. 1, 2004.

Kumar, Anand T.N., et al., "Fluorescence-Lifetime-Based Tomography for Turbid Media", Optics Letters, vol. 30, No. 24, pp. 3347-3349, Dec. 15, 2005.

Lam, S. et al., Time Domain Fluorescent Diffuse Optical Tomography: Analytical Expressions, Optics Express, vol. 13, No. 7, pp. 2263-2275, Apr. 4, 2005.

Leibert, Adam et al., "Evaluation Of Optical Properties Of Highly Scattering Media By Moments Of Distributions Of Times Of Flight Of Photons", Applied Optics, vol. 42, No. 28, pp. 5785-5792, Oct. 1, 2003.

Ntziachristos, Vasilis et al., "Experimental Three-Dimensional Fluorescence Reconstruction of Diffuse Media By Use Of A Normalized Born Approximation", Optics Letters, vol. 26, No. 12, pp. 893-895, Jun. 15, 2001.

Sevick-Muraca, Eva et al., "Origin Of Phosphorescence Signals Reemitted From Tissues", Optics Letters, vol. 19, No. 23, pp. 1928-1930, Dec. 1, 1994.

* cited by examiner

METHOD AND DEVICE FOR 3D RECONSTRUCTION OF THE DISTRIBUTION OF FLUORESCENT ELEMENTS

CROSS-REFERENCE TO RELATED PATENT APPLICATION OR PRIORITY CLAIM

This application claims the benefit of a French Patent Application No. 06-07065, filed on Aug. 2, 2006, in the French Intellectual Property Office, the disclosure of which is incorporated herein in its entirety by reference.

TECHNICAL FIELD AND PRIOR ART

This invention relates to the field of fluorescence molecular imaging on biological tissue by time-resolved optical methods.

It applies in particular to optical molecular imaging on small animals and optical molecular imaging on humans (brain, breast, and other organs where fluorophores can be injected).

The optical fluorescence molecular imaging optical techniques are now being increasingly developed owing to the use of specific fluorescent markers. These bind preferentially to the target cells of interest (for example cancer cells) and provided better detection contrast than non-specific markers. These techniques are designed to spatially locate the fluorescent markers, but also to determine the concentration thereof.

Optical tomography systems use various light sources. There are therefore continuous-mode apparatuses, frequency-mode apparatuses (that use frequency-modulated lasers) and finally apparatuses operating in temporal mode, which use pulsed lasers.

The time data is the data that contains the most data content on the traversed tissue, but for which the reconstruction techniques are the most complex. The measurement at each acquisition point is indeed a time-dependent function (called TPSF for "Temporal Point Spread Function").

It is sought to extract simple parameters of the TPSF, of which the theoretical expression is known. Then, the resolution of the reverse problem makes it possible to find the distribution of the fluorescent markers.

In document WO 2006/032151, the first three moments of the time curves, which are called "normalised moments" because they are the moments of the curves normalised by the excitation curve, are extracted.

Now, the moments of the time curves are dependent on the knowledge of the fluorescence lifetime. Consequently, in this document, to solve the reverse problem, the fluorescence lifetime is assumed to be known. However, this lifetime can be sensitive to the environment and is difficult to measure in vivo. A poor choice of this parameter leads to erroneous results.

The article of A. T. N. Kumar et al. "Fluorescence lifetime-based tomography for turbid media," Opt. Lett. 30(24), 3347-3349 (2005) describes a method that reconstructs one or more lifetimes. In fact, it is based on the determination of different lifetimes on the decay curves; then on a reconstruction based on their respective amplitudes. An approximation on the lifetime is made at the outset. This technique is particularly advantageous if there are two clearly distinct lifetimes.

The article "Time-Domain Fluorescence Molecular Tomography Based on Generalized Pulse Spectrum Technique", Fen Gao, Wei Liu et al., Proceedings BIOMED 2006 describes a method based on the Laplace transforms of the time curves at two frequencies, which requires two reconstructions, one on the concentration and the other on the lifetime. This method is more complex and costly in calculation time because it is based on numerical calculations to obtain the Laplace transforms (the analytical expression is not easy to find).

Therefore, there is the problem of determining the spatial distribution of fluorophores in a diffusing medium, without prior knowledge of the fluorescence lifetime.

DESCRIPTION OF THE INVENTION

The invention first relates to a method for processing emitted fluorescence signals, after excitation by radiation from a radiation source, by at least one fluorophore with a lifetime $\tau$ in a surrounding medium, which signals are detected by detection means, and which method comprises:
- the detection of a plurality of fluorescence signals ($\Phi_{fluo}$) emitted by the fluorophore(s) in the surrounding medium, each signal corresponding to a relative position, on the one hand of the fluorophore(s) and on the other hand of the source and the detection means,
- the calculation, based on these detected fluorescence signals, of values of a variable, independent of $\tau$ but dependent on the position or the spatial distribution of fluorophores in said medium,
- the determination of the position or the spatial distribution of fluorophores in said medium on the basis of the values of said variable.

The fluorophore(s) can be bonded to biological tissue, for example target cells of interest (for example cancer cells).

The detection of the signal(s) is preferably performed in a measurement window making it possible to recover almost all of the photons emitted by the fluorescence. The calculation of the values of a variable independent of the lifetime can therefore be done by taking into account the entirety of the signal(s) detected in this measurement window.

A method according to the invention can, for example, be performed without the fluorescence lifetime by considering a normalised measurement, for example to the measurement that gives the shortest fluorescence lifetime.

The variable independent of $\tau$ can also result from a normalised frequency function, for example with respect to a specific fluorescence signal.

This method can be adapted to transformations other than the mean time (for example, the Mellin-Laplace transforms), which make it possible to do without the lifetime owing to the normalisation.

According to an embodiment, said variable independent of $\tau$ results from the difference between the mean time $\tau$ calculated for each fluorescence signal and the mean time calculated for a specific fluorescence signal, preferably that for which the calculation time is minimal.

According to another embodiment, the independent variable results from the Mellin-Laplace transforms of the fluorescence signals.

The determination of the position or the spatial distribution of fluorophores in the medium can be achieved by a method of reversal using values of the variable. The reversal method can result from the minimisation of an error function between the measurement and said variable, for example using a simplex method.

According to another embodiment, the determination of the spatial distribution of fluorophore in said medium implements the resolution of a system of linear equations:

$$M = P \times C,$$

where M is a measurement column vector, P is a weight matrix and C is a distribution column vector.

According to the invention, it is possible to calculate the first moment of the curve of the fluorescence signal as a function of time.

A method according to the invention can also comprise a preliminary step of measuring the fluorescence signal emitted by the surrounding medium, in the absence of fluorophore, then a step of correcting the fluorescence signals ($\Phi_{fluo}$) emitted by the fluorophore in its surrounding medium.

The invention also relates to a device for processing fluorescence signals emitted by at least one fluorophore, with a lifetime τ in a surrounding medium, comprising:
- a source of radiation for excitation of said fluorophore,
- detection means for detecting a fluorescence signal emitted by said fluorophore,
- means for performing a relative movement of the source and the detection means with respect to the fluorophore,
- means for calculating values of a variable independent of τ, on the basis of a plurality of fluorescence signals ($\phi_{fluo}$) emitted by the fluorophore into its surrounding medium, with each signal corresponding to a relative position, on the one hand of the fluorophore and on the other hand of the source and the detection means,
- means for determining the position (in the case of a single fluorophore) or the spatial distribution (in the case of a plurality of fluorophores) of fluorophore(s) in said medium on the basis of the values of said variable.

The detection means are, for example, of the TCSPC type or camera-type means.

A device according to the invention can also comprise means for visual or graphic representation of the position or the spatial distribution of the fluorophore(s).

The variable independent of τ can result from a normalised frequency function, with respect to a specific fluorescence signal.

According to an embodiment, the variable that is independent of τ results from the difference between the mean time τ calculated for each fluorescence signal and the mean time calculated for a specific fluorescence signal.

This specific fluorescence signal is advantageously the one for which the mean time calculated is minimal.

According to an embodiment, the means for determining the position or the spatial distribution of fluorophores in the medium implement a minimisation of an error function of the values of said variable, which minimisation can be a processing operation by adjustment using a simplex method.

DETAILED DESCRIPTION OF SPECIFIC EMBODIMENTS

Figure 1A:
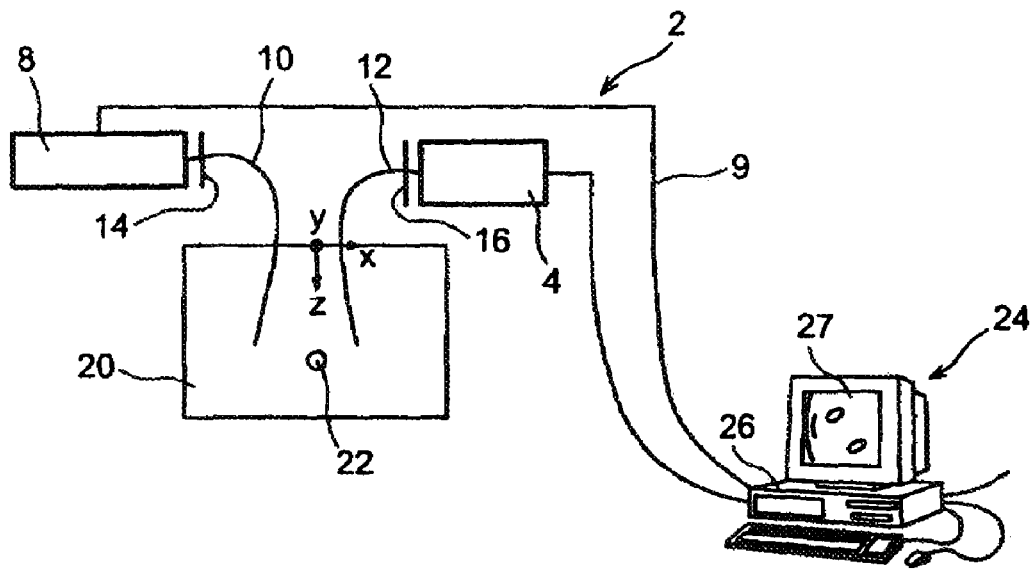
FIGS. 1A and 1B each show an example of an experimental device for implementing the invention.

FIG. 1A is an example of an experimental system 2 using, as a detector 4, a photomultiplier and a TCSPC (Time Correlated Single Photon Counting) card, actually integrated in an assembly of data processing means 24.

The light is transmitted by a pulsed radiation source 8, sent and collected by fibres 10, 12, which can be moved. The two fibres can be mounted on means for vertical and horizontal translation movement (according to the X and Y axes of FIG. 1). The distance d between the fibres is, for example, around 0.2 cm.

The radiation pulse source 8 can also be used as means for activating the TCSPC card (see the link 9 between the source 8 and the means 24).

According to a specific embodiment, the source 8 is a pulsed laser diode, with a wavelength of 631 nm and a repetition rate of 50 MHz.

The laser light preferably passes through an interference filter 14 so as to remove any light with a wavelength higher than the excitation wavelength.

The fibre 12 collects the light coming from the medium 20 studied. An interference filter 16 and a coloured filter absorbing the high wavelengths can be placed in front of the detector 4 so as to select the fluorescent light (for example: λ>650 nm, with the source being at the wavelength 631 nm) of a fluorophore 22 placed in the medium 20 and to optimise the elimination of the excitation light.

According to the TCSPC technique (for "Time Correlated Single Photon Counting"), using a photomultiplier, a photon emitted by the fluorophore after a radiation source pulse, is detected.

The system therefore enables time-resolved detection of fluorescence pulses. It makes it possible to recover almost all of the fluorescence photons.

Figure 2A:
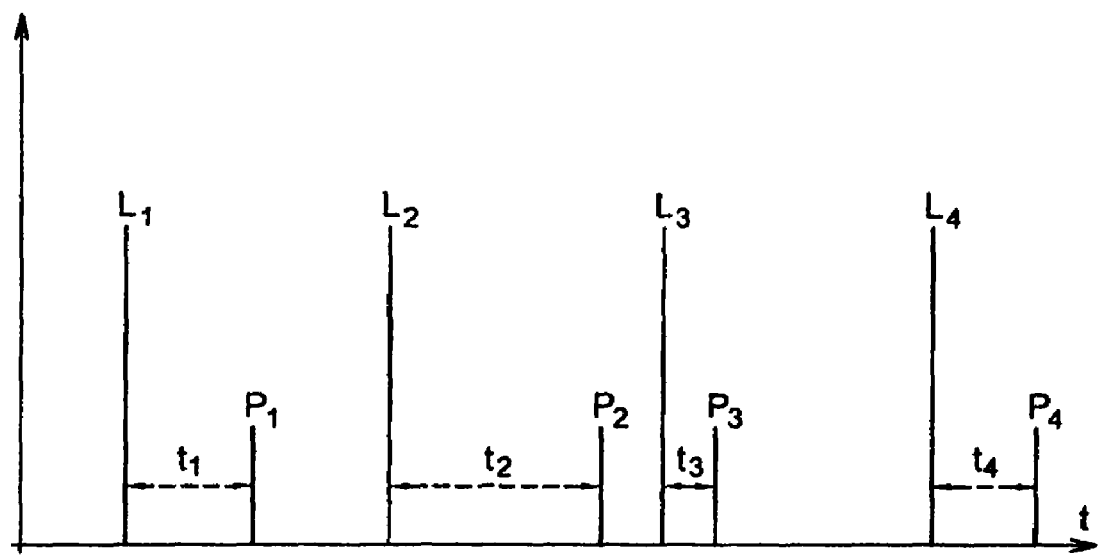
FIGS. 2A and 2B respectively show a series of laser pulses and single photons emitted, and a fluorescence curve obtained on the basis of data relating to the single photons.

FIG. 2A shows a series of laser pulses Li (i=1–4) and a series of corresponding single photons pi (i=1–4). Each photon is in fact detected with respect to the start of the corresponding pulse: in FIG. 2A, ti represents the time lapsed between each laser pulse Li and the time of detection of each photon pi.

Figure 2B:
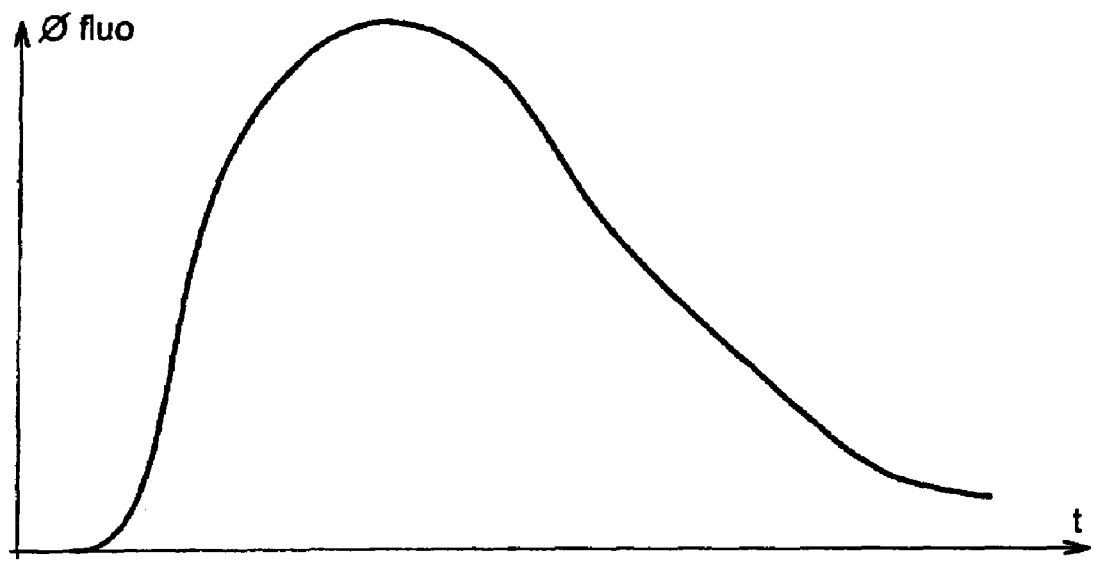

It is then possible therefore to establish a statistical distribution, as shown in FIG. 2B, of the number of fluorescence photons detected, as a function of the time lapsed t with respect to each laser pulse. Such a curve $\Phi_{fluo}(t)$, which, as seen (also in FIGS. 3, 5 and 7), makes it possible to use all of the data in a large time window, on each side of the maximum intensity point (and not only in the rising portion of the signal) can then be processed so as to obtain the characteristic data as will be explained below.

Electronic means 24 such as a microcomputer are programmed to store and process the data of the TCSPC card. More specifically, a central unit 26 is programmed to implement a processing method according to the invention. Display or viewing means 27 make it possible, after processing, to show the positioning of or the spatial distribution of fluorophores in the medium 20 examined.

Other detection techniques can be used, for example an ultra-fast intensified camera of the "gated camera" type; in this case, the camera is opened in a time gate, with a width for example around 200 ps, then this gate is shifted, for example from 25 ps to 25 ps.

Figure 1B:
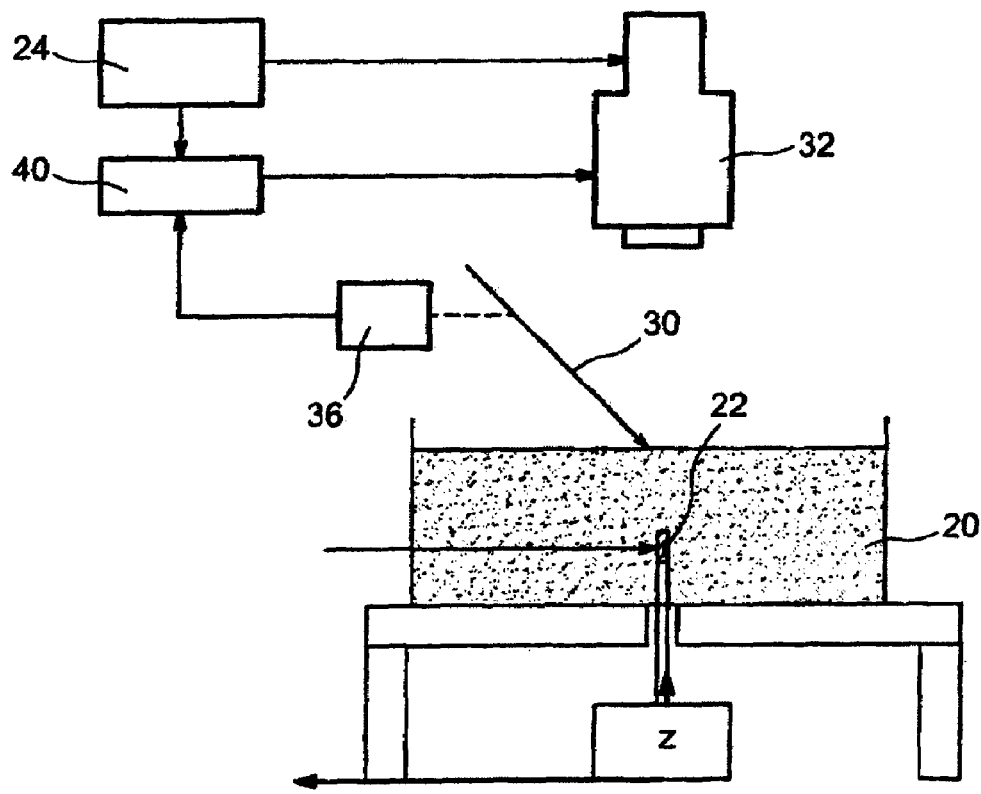

FIG. 1B is an example of another experimental system 2 using, as a detector 32, a fast camera. A beam 30 for excitation of the fluorescence of a medium 20, containing one or more fluorophores 22, is emitted by a radiation source (not shown in the figure), which can be of the same type as that shown above in association with FIG. 1A. A photodetector 36 makes it possible to control means 40 forming a delay line. Reference 24 designates, as in FIG. 1A, electronic data processing means of the microcomputer type, programmed to store and process the data of the camera 32. A central unit for these means 24 is programmed to implement a processing method according to the invention. Again, display or viewing means make it possible, after processing, to show the positioning or the spatial distribution of fluorophores in the medium 20 examined.

It is also possible to work with pulses in the femtosecond domain, on the condition that there is an adequate radiation source, i.e. a laser source 8 of which each pulse has a time width also in the femtosecond domain.

A simple preliminary measurement makes it possible to measure the response (the abbreviation IRF for "Instrument Response Function" will hereinafter be used) of the device: the two fibres 10, 12 separated by a predetermined distance are aligned, and a pulse is transmitted from the first fibre 10 to the second fibre 12. The signal obtained at the output of the second fibre 12 provides the IRF response. The width a mid-height of this signal, in consideration of the distances used, can be on the order of some dozens of ps, around 80 ps in the example provided.

A phantom can be used, containing distilled water in which a China ink (of Dalbe, France) is added as an absorbent medium, and "intralipid" (of Fresnius, France) is added as a diffusing medium. The relative concentrations are adjusted to the level of the parameters of the biological tissues. The phantom is contained in a plastic cylinder with a diameter of 11 cm and a height of 10 cm. A volume of 1 μl of fluorophore Cy5 (of Amersham) at a concentration of around 10 μmol.L-1 is placed at the end of a thin glass capillary tube 21 (see FIG. 1B) (length 3 cm and thickness 1 mm). The tube is inserted into the phantom through a hole. The optical properties of the phantom and the lifetime of the fluorophore are measured by TCSPC-type techniques (single photon counting) and are presented in table I below.

TABLE I

| $\mu_a$ | $\mu_s'$ | $\tau$ |
|---|---|---|
| 0.0534 cm$^{-1}$ | 11.82 cm$^{-1}$ | 1.02 ns |

In the measurements, the fibres are added at around 2.5 cm to the medium 20, which makes it possible to approach the geometry of an infinite medium.

Scans performed using computer means 24 (with software such as Labview), which simultaneously control the fibre movement means and the TCSPC card (or the camera 32 of FIG. 1B) with a parallel communication port.

We will first discuss the example of an infinite medium with a single fluorophore.

We will consider a single fluorophore M in the medium, at an (unknown) position identified by a vector r at the point OXYZ. The excitation source (or rather the end of the fibre 10, on the fluorophore side) is located at $r_s$ and the detector (or rather the end of the fibre 12, on the fluorophore side) in position $r_d$. The pulse transmission time is designated by $t_0$.

The source-fluorophore distance is denoted $|r_s-r|=r_{sr}$ and the fluorophore-detector distance is denoted $|r-r_d|=r_{rd}$.

In the time domain, the flow of excitation photons at the time t" is denoted $\phi_x(r_{sr},t"-t_0)$. The index x corresponds to the excitation wavelength $\lambda_x$. The fluorophore 22 absorbs the excitation light and re-emits the fluorescence light at time t', wavelength $\lambda_m$, and with a time decay τ. The expression of the photon flow emitted by the fluorophore located at r at the time t' is the convolution of the propagation function $\phi_x$ and the time decay of the fluorescence:

$$S_f(r_{sr}, t') = \alpha \int_0^{t'} \phi_x(r_{sr}, t" - t_0) \frac{1}{\tau} \exp\left(-\frac{t'-t"}{\tau}\right) dt" \quad (1)$$

Where α is scale factor that is dependent on the power of illumination, the quantum efficiency of the fluorophore.

The equation 1 gives the temporal expression of the intensity of the radiation emitted by the fluorophore. This radiation will then be detected by the detector 4 (in this case also, it is the end of the fibre, on the side of the medium 20), in position $r_d$, at the time t, after having transited from the fluorophore 22 to this same detector. The resulting flow of fluorescence photons is proportional to a double convolution:

for the propagation from the source to the fluorophore: the convolution of $\phi_x$ (at the excitation wavelength) with the fluorescence decay time, with this first convolution leading to the above expression $S_f$ (equation (1)), and, then, that of $S_f$ (given by the equation (1)) with $\phi_m$ (at the emission wavelength), for the propagation of the fluorophore to the detector.

It is therefore possible to write the detected flow of fluorescence photons:

$$\phi_{fluo}(r_{sr}, r_{rd}, t) = \alpha \int_0^t S_f(r_{sr}, t', t_0) \phi_m(r_{rd}, t-t') dt' \quad (2)$$

$$= \alpha \int_0^t \int_0^{t'} \phi_x(r_{sr}, t' - t_0) \frac{1}{\tau} \exp\left(-\frac{t'-t"}{\tau}\right) \phi_m(r_{rd}, t - t') dt' dt".$$

To have a simplified solution, it is possible to use the solution for an infinite medium, with the approximation that the optical coefficients are the same in excitation and in emission. The expression obtained is the following:

$$\phi_{fluo}(r_{sr}, r_{rd}, t) = \alpha \int_0^t dt_e \frac{r_{sr} + r_{rd}}{r_{sr} r_{rd}} \frac{1}{[4\pi c(t-t_e)]^{3/2}} \quad (3)$$

$$\exp[-\mu_a c(t-t_e)] \exp\left[-\frac{(r_{sr}+r_{rd})^2}{4cD(t-t_e)}\right] \frac{\exp(-t_e/\tau)}{\tau}$$

Where $\mu_a$ is the absorption coefficient and D is the diffusion coefficient. For a plurality of fluorophores, we use, as indicated below, an integral on the volume, and we assume a low-absorbing medium since this model does not take into account a possible reabsorption and a possible diffusion.

This theoretical function $\Phi_{fluo}$ corresponds to the curve, obtained by experimental measurements, of FIG. 2B. A data processing operation, for example a calculation of certain parameters, can be performed by taking data in an entire time interval, from the start of the rising portion of the curve to the end of the falling portion, or at least by taking values in an interval on each side of the maximum of the curve, for example a time interval of which the threshold values are those corresponding substantially to at least x % of the maximum intensity of the curve, with x for example being capable of being equal to 1 or 5 or 10. In particular, it is possible on the basis of such data to calculate the moments of any order 0, 1, ... n (n>1).

It is possible in particular to extract from this function, therefore equation 3, the mean time (or the first moment). For a distribution function g(t), the mean time is given by:

$$\langle t \rangle = \frac{\int_{-\infty}^{\infty} t g(t) dt}{\int_{-\infty}^{\infty} g(t) dt} \quad (4)$$

As shown, this first moment, like the moment of 0 order, can be calculated by taking into account the entirety, or almost, of the signal detected, or the fluoroscence function, in a large measurement window, and not only in the rising portion of the fluorescence curves.

To develop this formula, let us consider, rather than the temporal expression of the flow, its frequency expression:

$$\Phi_{fluo}(r_{sr}, r_{rd}, \omega) = \alpha' \frac{\exp[ik(r_{sr} + r_{rd})]}{r_{sr} + r_{rd}} \frac{1}{1 - i\omega\tau} \quad (5)$$

Where α' is a constant independent of the frequency and $k^2 = -\mu_a/D + i\omega/(cD)$. Then, by using the following formula:

$$\langle t \rangle = i \frac{\partial \Phi}{\partial \omega}\bigg|_{\omega=0} \times \frac{1}{\Phi(\omega)|_{\omega=0}} \quad (6)$$

the analytical expression of the theoretical mean time can be found:

$$\langle t \rangle_{theo} = \frac{r_{sr} + r_{rd}}{2c\sqrt{\mu_a D}} + \tau \quad (7)$$

In this expression, the lifetime τ of the fluorophore appears. The unknown position r is contained in the expressions of $r_{sr}$ and $r_{rd}$.

The processing of experimental data will now be described.

First, the calculation of the mean time on the experimental data can be sensitive to the disturbances due to the excitation light or to the fluorescence of the medium surrounding the fluorophore, which occur when the fluorescence signal is low. In particular, the excitation light that arrives first can reduce the mean time of the signal. To correct this disturbance, the signal can be measured, but without fluorophore.

This measurement without fluorophore is designated by $mesure_{IL}$ and is composed:
   partially by the excitation light that passes through the filters,
   and partially (long portion of the signal) by the fluorescence of the surrounding medium, or the phantom without fluorophore.

This measurement can be subtracted from the data measured with fluorophore ($mesure_{fluo}$), if it is desirable to correct the residual light data and obtain the real signal, designated by $signal_{fluo}$ (to indicate the difference with a direct measurement, see equation 8). The subtraction also makes it possible to suppress the background noise. By taking into account the expressions of the detection times (respectively $T_{fluo}$ for $mesure_{fluo}$ and $T_{IL}$ for $mesure_{IL}$), the fluorescence signal can be expressed as follows:

$$signal_{fluo} = mesure_{fluo} - \frac{T_{fluo}}{T_{IL}} mesure_{IL} \quad (8)$$

Figure 3:
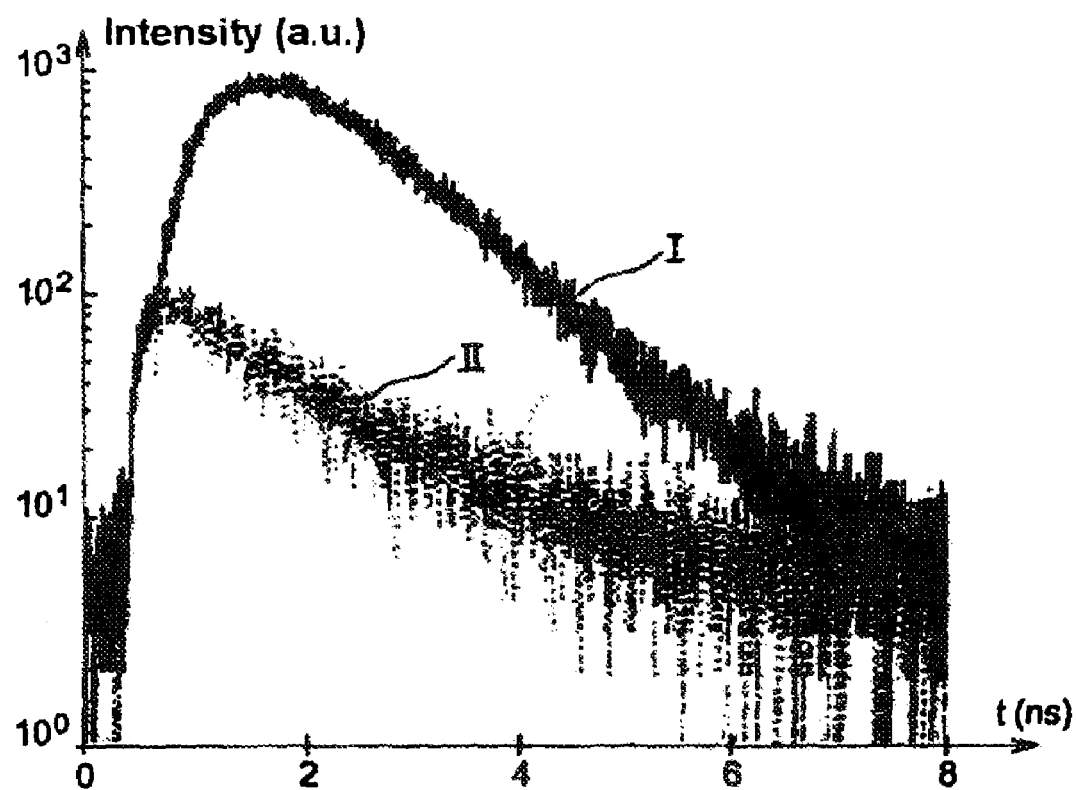
FIG. 3 shows examples of fluorescence time decay curves, with and without fluorophore.

FIG. 3 gives the signal with fluorophore (curve I) and without fluorophore (curve 11) for an inclusion at a depth z=0.74 cm. The ends of the fibres turned toward the medium 20 are separated by 0.2 cm.

For the calculation of the first moment, the integration threshold values are defined by times defined by 1% of the time corresponding to the maximum amplitude of the TPSF, for the upper and lower limit, so as to remove the background noise in accordance with the study of A. Liebert et al. "Evaluation of optical properties of highly scattering media by moments of distributions of times of flight of photons" Applied optics, vol. 42, No. 28, 5785-5792 (2003).

More generally, the invention makes it possible to measure a signal in a large time window, extending on each side of the time corresponding to the maximum of the intensity signal as a function of time. The time data on each side of this maximum can be used to calculate the various moments to be calculated.

To compare the mean time of the signal $\langle t \rangle_{signal}$ with the theoretical mean time [equation 7], the IRF (function already defined above) can be taken into account. The signal is the convolution of the IRF with the theoretical response or the specific response of the diffusing medium. The properties of the first moment show that the experimental mean time can be written as the sum of the theoretical mean time $\langle t \rangle_{theo}$ and the mean time of the IRF $\langle t \rangle_{IRF}$:

$$\langle t \rangle_{signal} = \langle t \rangle_{theo} + \langle t \rangle_{IRF} \quad (9)$$

Figure 4:
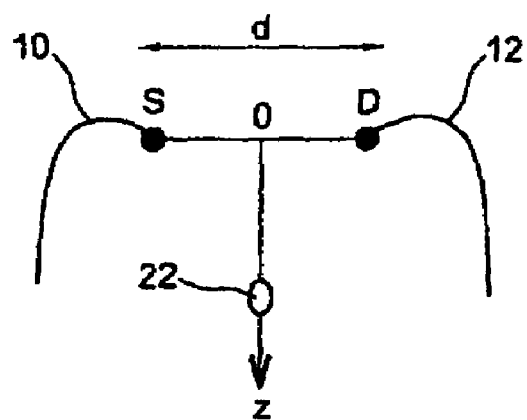
FIG. 4 diagrammatically shows the relative position of a source-detector pair and the inclusion of s.

The reverse problem, i.e. determining the position of the inclusion as a function of the measurements, can be solved for measurements above the inclusion (see FIG. 4, which shows the geometry of the ends of the fibres 10, 12 and the position of the fluorophore 22). As the inter-fibre distance is low (d=0.2 cm), it can be assumed that $r_{sr}+r_{rd} \approx 2z$, where z represents the depth of the inclusion under the fibres. It is therefore possible to rewrite the equation 9:

$$\langle t \rangle_{signal} = \frac{r_{sr} + r_{rd}}{2c\sqrt{\mu_a D}} + \tau + \langle t \rangle_{IRF} = \frac{z}{c\sqrt{\mu_a D}} + \tau + \langle t \rangle_{IRF} \quad (10)$$

This expression can be reversed to obtain z when the optical parameters, the lifetime and the mean time of the IRF are known:

$$z = c\sqrt{\mu_a D} (\langle t \rangle_{signal} - \tau - \langle t \rangle_{IRF}) \quad (11)$$

However, this method can be used only if the ends of the fibres 10, 12 are placed exactly above the inclusion so as to satisfy the assumption $r_{sr}+r_{rd} \approx 2z$ and to determine the lifetime and the mean time of the IRF.

To avoid this initial knowledge of the inclusion position, the lifetime and the mean time of the IRF, a more general method has been developed to determine a completely unknown position.

A scanning is performed above the inclusion for N relative fluorophore—fibre positions. The relative position of two fibres, therefore of one fibre with respect to tile other, preferably remains constant. The mean time, $\langle t \rangle_{signal,i}$, $i \in [1,N]$, is calculated for each position of the scanning. Then, another mean time, preferably the lowest: $\min(\langle t \rangle_{signal,i})$ is selected and subtracted from each mean time. This choice is justified by the fact that this lowest time corresponds to the measurement position closest to the inclusion with the best signal-to-noise ratio. Then, $\Delta \langle t \rangle_{signal,i}$ is considered to be the new variable:

$$\Delta \langle t \rangle_{signal,i} = \langle t \rangle_{signal,i} - \min(\langle t \rangle_{signal,i}), \; i \in [1, N]) \quad (12)$$

$$= \frac{r_{sr,i} + r_{rd,i}}{2c\sqrt{\mu_a D}} - \frac{r_{sr,min} + r_{rd,min}}{2c\sqrt{\mu_a D}}$$

This new variable is independent of the lifetime and the mean time of the IRF due to the difference performed. It is instead dependent on the position or the spatial distribution of the fluorophore. In the case of a single fluorophore, this position of the inclusion, of coordinates (x, y, z), is then defined as the one enabling the error function $\chi^2$ to be minimised.

$$\chi^2(x, y, z) = \sum_i (\Delta \langle t \rangle_{signal,i} - \Delta \langle t \rangle_{theo,i})^2 \quad (13)$$

The input variables are the values of $\Delta \langle t \rangle_{signal,i}$ extracted from the measurements. They are compared to the theoretical formula where $\Delta \langle t \rangle_{theo,i}$ is given by:

$$\Delta \langle t \rangle_{theo,i} = \langle t \rangle_{theo,i} - \min(\langle t \rangle_{theo,j}), \; i \in [1,N]) \quad (14)$$

Where j is the index that identifies the experimental signal that has the shortest mean time. The adjustment procedure is, for example, based on a simplex method such as that described in the article of J. C. Lagarias et al. "Convergence properties of the Nelder-Mead simplex method in low dimensions", SIAM Journal on Optimization, vol. 9(1), p. 112-147, 1998.

Experimental results will be presented, which make it possible to validate the model above. Then, we will present measurements that can, with the method according to the invention, solve the reverse problem, i.e. determine the position of the inclusion.

Figure 5:
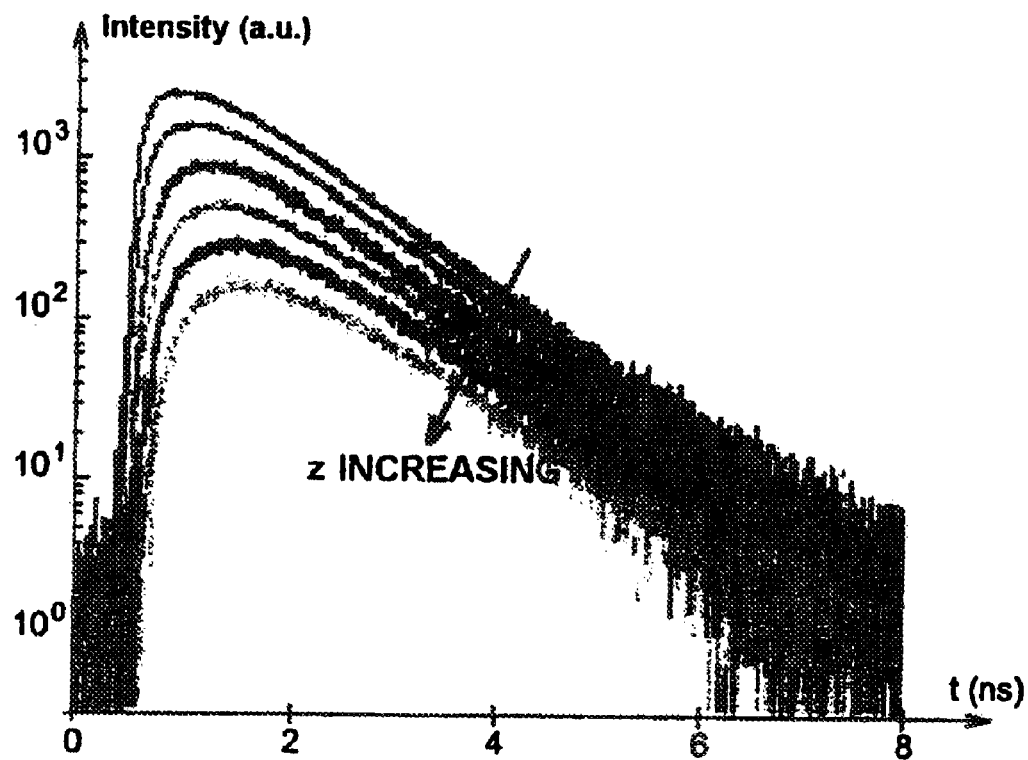
FIG. 5 shows fluorescence data for various positions of a fluorophore under excitation and detection fibres.

Time-resolved signals for an interfibre distance of 0.2 cm and for inclusions at different depths under the fibres (z=0.24; 0.34; 0.44; 0.54; 0.64; 0.74 cm) are presented in a semi-logarithmic scale in FIG. 5.

The amplitudes are shown in this figure in an arbitrary scale. In this representation, the exponential decay of the fluorescence of Cy5 appears to tend toward a straight line. The more the depth z increases, the more the time position of the maximum is shifted toward the long times, due to the longer path of the photons.

The theoretical expression of the mean time was first validated. The mean time of the IRF was subtracted from the mean time measured so as to perform a comparison with the theoretical formula of equation 9.

Figure 6:
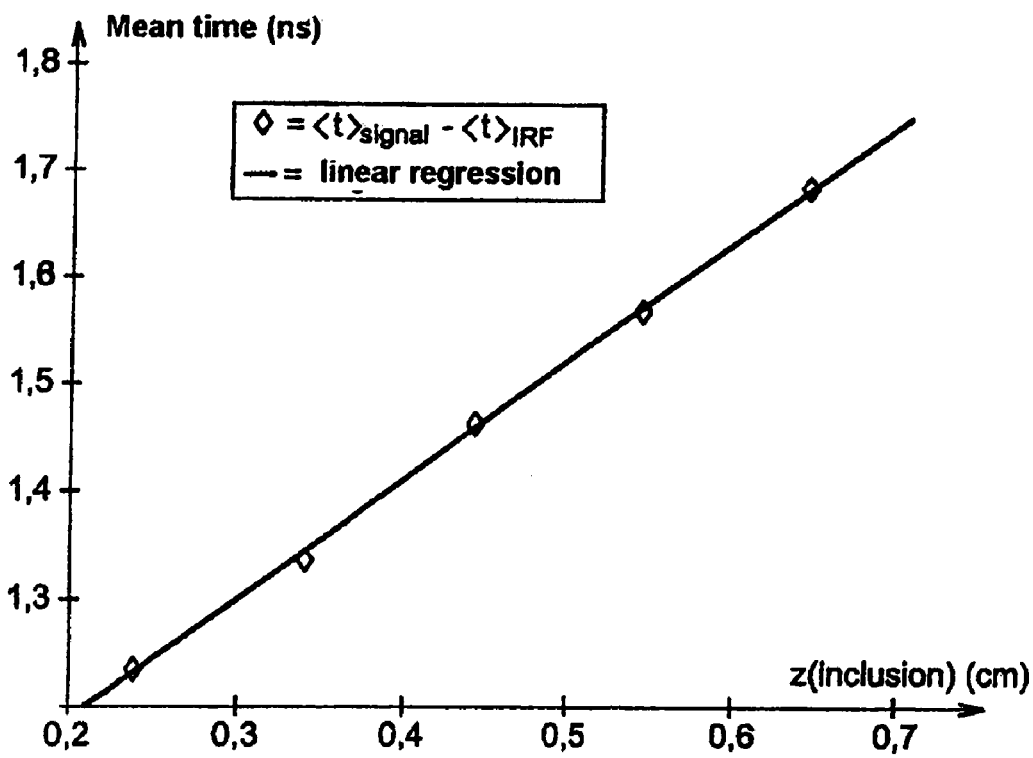
FIG. 6 shows mean times calculated on the basis of fluorescence measurements for various positions or depths of a fluorophore.

FIG. 6 shows the corrected experimental mean time of the instrument response ($=\langle t \rangle_{signal} - \langle t \rangle_{IRF}$) as a function of the depth z of the inclusion. In accordance with the theoretical expression (equation 10), the mean time is a linear function of the inclusion position. The slope measured experimentally is 1.14, equal to the theoretical slope $$(c\sqrt{\mu_a D})^{-1}$$

calculated on the basis of the equation (10) with the optical coefficients of the medium.

The ordinate at zero, 0.96 ns, is relatively close to the measured lifetime ($\tau$=1.02 ns).

Then, the fluorescence model was tested to determine whether it corresponds to the measurements. The solution calculated (equation 3 with the parameters of table I) is convoluted with the IRF and compared with the measurements. The curves are normalised at the same surface as the experimental curve on an arbitrary time interval (1% of the maximum on the right and left sides).

Figure 7:
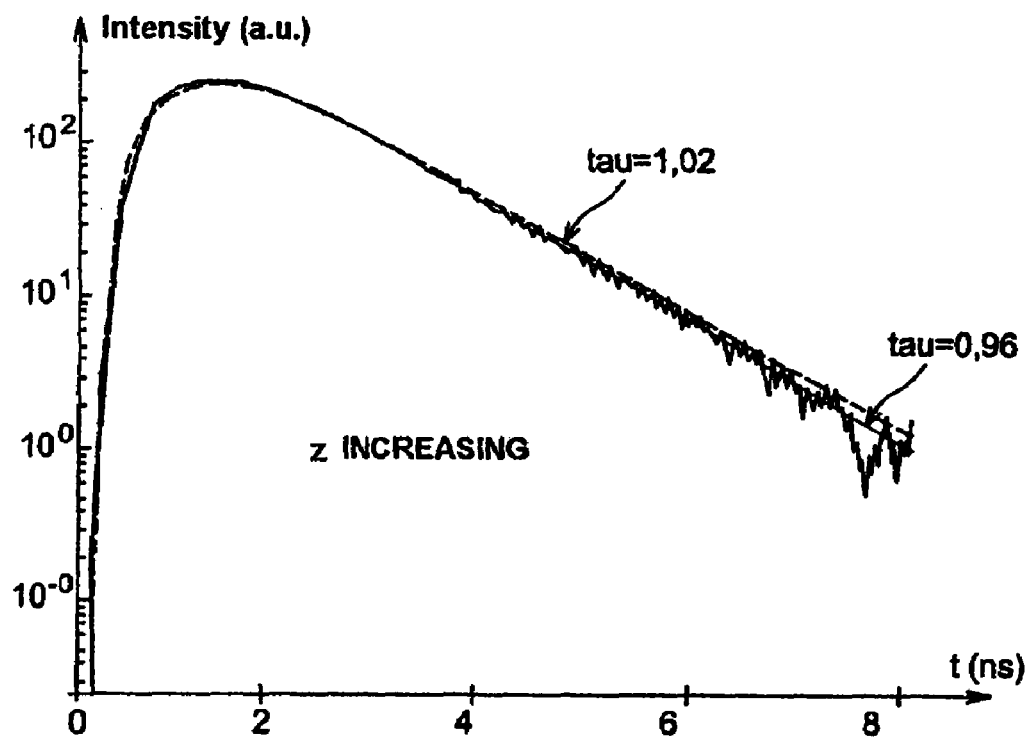
FIG. 7 shows three fluorescence time decay curves, one resulting from a measurement and two from simulations.

FIG. 7 shows the experimental results for a fluorophore at the depth z=0.74 cm and two simulations for two different lifetimes (0.96 ns: solid line curve, 1.02 ns: dotted line curve). A good conformity is found between the simulations and the experimental results.

Table II below presents the results of the reversal formula for $\tau$=0.96 ns and $\tau$=1.02 ns. A good conformity is noted between the calculated and real values.

TABLE II

| $z$exp (cm) | 0.24 | 0.34 | 0.44 | 0.54 | 0.64 | 0.74 |
|---|---|---|---|---|---|---|
| z calculated ($\tau$ = 0.96 ns) | 0.24 | 0.33 | 0.45 | 0.54 | 0.64 | 0.74 |
| z calculated ($\tau$ = 1.02 ns) | 0.19 | 0.28 | 0.40 | 0.49 | 0.59 | 0.69 |

The resolution of the reverse problem will be illustrated for various inclusion depths using measurement grids.

Figure 8:
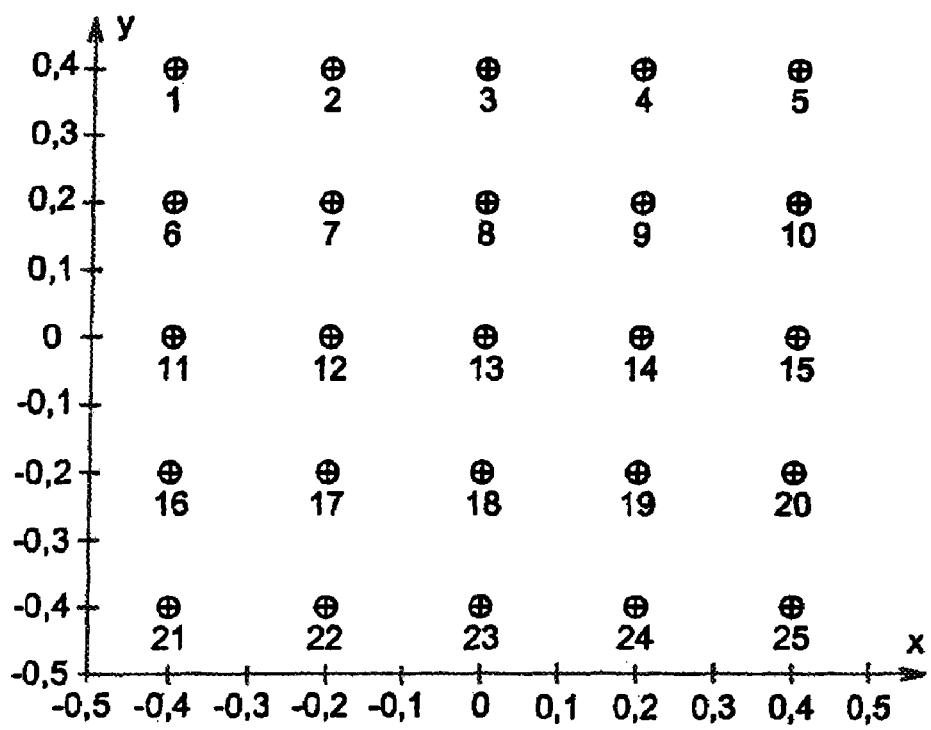
FIG. 8 shows a grid of detectors.

The sampling is performed with a measurement grid comprising 5×5 detectors arranged at a pitch of 0.2 cm. The grid is positioned above the inclusion. FIG. 8 shows the detector grid. The emission fibre 10 is −0.2 cm (according to axis x) from the detection fibre 13. The inclusion is centred at (0, 0) and placed at various depths. The centre (0, 0) corresponds to the collection fibre 12.

Figure 9:
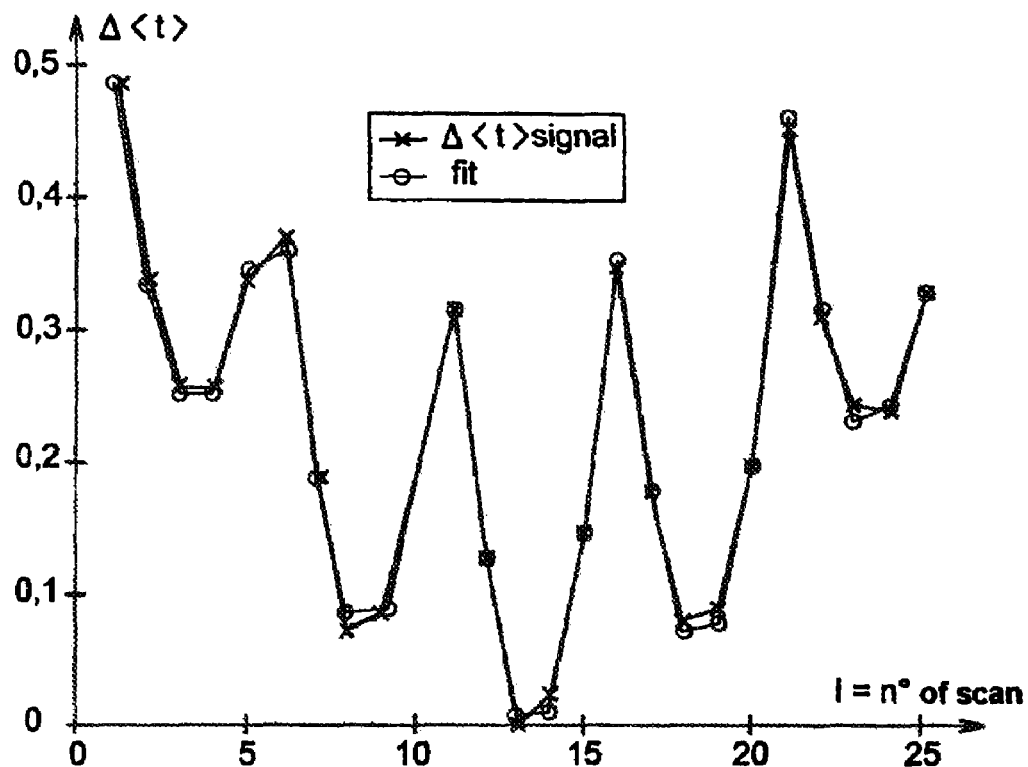
FIG. 9 shows the change in detection mean times for various positions of the detector-fluorophore assembly.
Figure 10:
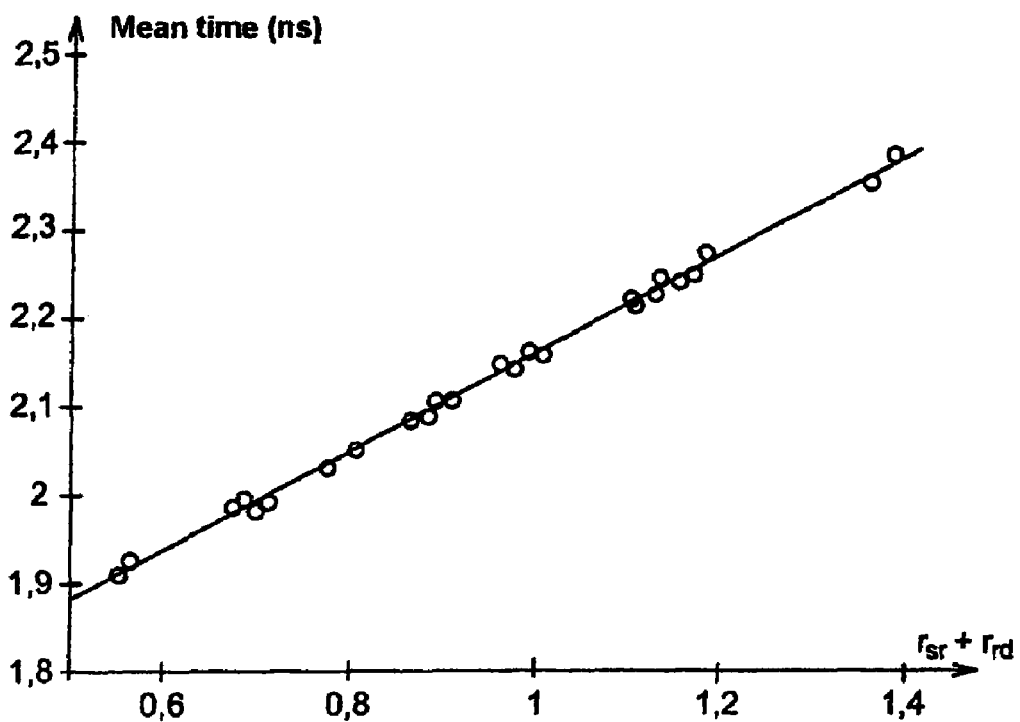
FIG. 10 shows the change in detection mean times as a function of the total optical path covered by the photons.

The adjustment procedure is applied to the data obtained from all of the detection points. For the first depth (0.24 cm), for example, the experimental value of the experimental differential mean time ($\Delta \langle t \rangle_{signal}$) and the differential mean time calculated by adjustment are shown in FIG. 9. FIG. 10 shows the mean time as a function of $r_{sr}+r_{rd}$ (photon path), for an inclusion positioned at z=0.24 cm. Table III shows the results of the adjustment for each inclusion depth and the slopes corresponding to the plotting of the mean time as a function of $r_{sr}+r_{rd}$. These slopes can be compared to the theoretical slope $$\frac{1}{2c\sqrt{\mu_a D}}, \quad [\text{Eq. (7)}]$$

calculated using the values of table I and equal to 0.572. The theoretical slope is therefore found, which is a confirmation of the validity of the model used. The device is that of FIG. 1A, but the fibres are separated by 2 mm and a scanning with a pitch of 2 mm is performed above the inclusion (the phantom has a volume of around 1 mm3). The position of the inclusion is identified with greater precision than the mm (200 μm for the set of measurements performed).

TABLE III

| z real (cm) | x (cm) | y (cm) | z (cm) | Slope |
|---|---|---|---|---|
| 0.24 | −0.01 | −0.01 | 0.24 | 0.572 |
| 0.34 | −0.02 | 0.01 | 0.33 | 0.577 |
| 0.44 | −0.02 | 0.02 | 0.42 | 0.578 |
| 0.54 | −0.02 | 0.04 | 0.53 | 0.577 |

Scans were performed with grids not centred on the inclusion.

The inclusion, initially positioned at z=0.3 cm under the fibres (initial position=(0; 0; 0.34)) was moved along the axis x toward two other positions: (−0.2, 0, 0.34) then (−0.4, 0, 0.34). The zero position is indicated only for comparison. As shown by table IV, which gives the positions obtained by adjustment, by comparison with the real positions, both the location (x, y) and the depth are correctly determined by the adjustment procedure for the three locations.

TABLE IV

| Real position | (0, 0, 0.3) | (−0.2, 0, 0.3) | (−0.4, 0, 0.3) |
|---|---|---|---|
| Position by adjustment | (−0.00, 0.00, 0.32) | (−0.20, 0.00, 0.32) | (−0.41, 0.00, 0.31) |

These tests show that the method does not require a priori knowledge of the inclusion position (x, y) and remains valid if the grid is shifted with respect to the inclusion.

As explained above in the case of a single fluorophore, the invention can also be applied to the case of a plurality of fluorophores, as will be shown below. In this second case, it is attempted to find the spatial distribution of the fluorophores in the medium 20. This spatial distribution is the quantity to be reconstructed in the context of the reverse problem. The same type of experimental device as that used for the single fluorophore, for example that of FIG. 1A or 1B, can be used in the case of a plurality of fluorophores.

To this end we will consider, as in the first case, the theoretical context of the approximation of the diffusion, in order to model the propagation of the light in the diffusing medium. The equation of the diffusion that gives the density of photons Φ for a homogeneous medium has the form:

$$\frac{1}{c_n}\frac{\partial \phi(r,t)}{\partial t} - D \cdot \nabla^2 \phi(r,t) + \mu_a \phi(r,t) = S(r,t) \quad (15)$$

where:
- $c_n$ is the propagation speed of the light in the medium. If the refraction index of the medium is noted, then $c_n = c/n$ with c being the propagation speed of the light in the vacuum;
- $D=1/[3(\mu_a+\mu'_s)]$ is the diffusion coefficient, where $\mu_a$ and $\mu'_s$ are the reduced absorption and diffusion coefficients of the medium.
- S is the source term.

In the frequency domain, the solution is written:

$$\Phi(r,\omega) = \frac{Q_0}{4\pi D}\frac{\exp(ikr)}{r} = \frac{Q_0}{4\pi D}G(r,\omega) \quad (16)$$

where $Q_o$ is a factor dependent on the power of the source, $$G(r,\omega) = \frac{\exp(ikr)}{r}$$

is the Green's function of the system and k is defined by the following relation:

$$k^2 = -\frac{\mu_a}{D} - \frac{i\omega}{cD} \quad (17)$$

Other models can also be used (radiative transfer model, random step model, or digital simulations of the Monte Carlo type, for example). This means that it is possible to calculate a Green's function in contexts other than the approximation of the diffusion.

Equations 15 and 16 above are the counterpart of the expression (1) given above in the case of a single fluorophore.

Let us consider a homogeneous diffusing medium that contains fluorophores.

A source pulse is transmitted in $r_s$ at $t_0$, and a detector is placed in $r_d$.

We note $\phi_x(|r-r_s|, t'')$ the photon density, which reaches the point r at t''. The index "x" indicates that the wavelength is that of the excitation source $\lambda_x$.

No hypothesis is necessary on the form of $\Phi_x$. It can be noted that, if the medium is infinite, $\Phi_x$ will have the form given by the solution (16) in an infinite medium.

A fluorophore placed in r will absorb this light $\Phi_x$ and emit fluorescence light at t', with a fluorescence lifetime τ (also called fluorescence decay) and an efficacy η. The photon density in τ at t' is the convolution of the propagation function $\Phi_x$ and the fluorescence decay:

$$\delta S_f(|r-r_s|, t') = \int_0^{t'} \phi_x(|r-r_s|, t''-t_0)\frac{\eta(r)C(r)}{\tau(r)}\exp\left(-\frac{t'-t''}{\tau(r)}\right)dt'' \quad (18)$$

We have denoted it as $\delta S_f$ because this term then becomes a source term at the emission wavelength $\lambda_m$, which will be propagated and detected in $r_d$ at t. C(r) is proportional to the concentration of fluorophores at point r. Hence, the expression of the final photon density $\delta\phi_{fluo}$, which is the convolution of the previous term and the propagation function Φ m between the inclusion and the detector:

$$\delta\phi_{fluo}(|r-r_s|,|r-r_d|,t) = \int_0^t \delta S_f(|r-r_s|,t')\phi_m(|r_d-r|,t-t')dt'$$

$$= \int_0^t \int_0^{t'} \phi_x(|r-r_s|,t''-t_0)\frac{\eta(r)C(r)}{\tau(r)}\exp\left(-\frac{t'-t''}{\tau(r)}\right)\phi_m(|r_d-r|,t-t')dt'\,dt'' \quad (19)$$

It is possible to adopt the following notations to simplify the writing:

$$r_{sr}=|r-r_s| \text{ et } r_{rd}=|r-r_d| \quad (20)$$

If there is a plurality of fluorophores in the medium, the integration is performed over the entire volume to obtain the final expression:

$$\phi_{fluo}(r_{sr},r_{rd},t) = \int_v dr \delta\phi_{fl}(r_{sr},r_{rd},t) \quad (21)$$

For this volume integration, any reabsorptions and diffusions by the other fluorophores that are not taken into account in this model are overlooked.

If the Fourier transform is performed on the previous expression, we obtain the expression of the fluorescence photon density $\Phi_f(r_s,r_d,\omega)$ in the frequency domain.

This expression has the advantage of being a bit simpler and more suitable for the subsequent calculations:

$$\Phi_f(r_{sr},r_{rd},\omega) = \int\int\int \Phi_x(r_{sr},\omega)\frac{\eta(r)C(r)}{1+i\omega\tau(r)}\Phi_m(r_{rd},\omega)dr^3 \quad (22)$$

The fluorescence time curves are measured for a set of relative positions on the one hand of the source-detector assembly and on the other hand of the medium 20. A data processing operation, for example a calculation of certain parameters, can be performed by taking data in an entire time interval, from the start of the rising portion of the curve to the end of the falling portion, or at least by taking values in an interval on each side of the maximum of the curve, for example a time interval of which the threshold values are those corresponding substantially to at least x% of the maximum intensity of the curve, with x for example being capable of being equal to 1 or 5 or 10. In particular, it is possible on the basis of such data to calculate the moments of any order 0, 1, ... n (n>1).

If we consider an infinite medium, at each point, the signal measured is proportional to the fluorescence photon density. The photon density can be assimilated to the signal by assigning it a proportionality coefficient, which is dependent only on instrumental factors (excitation power, detector gain, filter attenuation, etc.). The photon density is expressed as a function of this instrumental factor, diffusion coefficients D and Green's functions G, which are known (at both wavelengths, which are always indicated by the indices x and m).

$$\Phi_f(r_{sr},r_{rd},\omega) = \alpha \int\int\int_v \frac{1}{D_x D_m} G_x(r_{sr},\omega)\frac{\eta(r)C(r)}{1+i\omega\tau(r)} G_m(r_{rd},\omega)dr^3 \quad (23)$$

This equation can be discretised by changing to a sum over the voxels, where k represents the size of the discretisation pitch:

$$\Phi_f(r_{sr},r_{rd},\omega) = \alpha \sum_{v=\text{voxels}} \frac{1}{D_x D_m} G_x(r_{sr_v},\omega)\frac{\eta(r_v)C(r_v)}{1+i\omega\tau(r_v)} G_m(r_{r_vd},\omega)h^3 \quad (24)$$

It is approximated that the optical coefficients are the same at both wavelengths, and we therefore have: $D=D_x=D_m$.

Among all of the measurements, the source-detector pair is identified (denoted $r_{s_m}$-$r_{d_m}$), for which the mean time of the TPSF is the shortest: this measurement is denoted $\phi^{min}(r_{s_m},r_{d_m})$. It is preferably chosen with respect to others, because it has the largest amplitude, and therefore the best signal-to-noise ratio for a constant power of the excitation light on the acquisitions.

The new functions considered are now defined by:

$$\Phi^N(r_s,r_d,\omega) = \frac{\Phi_f(r_s,r_d,\omega)}{\Phi^{min}(r_{s_m},r_{d_m},\omega)} \quad (25)$$

For $\omega=0$, the above formula gives the expression of the moment of order 0, i.e. in fact the time integral of $\Phi_{fluo}$.

We can specify the expression of $\Phi^{min}(r_{s_m},r_{d_m})$:

$$\Phi^{min}(r_{s_m},r_{d_m},\omega) = \quad (26)$$
$$\alpha \sum_{v=\text{voxels}} \frac{1}{D^2} G_x(r_{s_m r_v},\omega)\frac{\eta(r_v)C(r_v)}{1+i\omega\tau(r_v)} G_m(r_{r_v d},\omega)h^3$$

where the factor $\alpha$ remains the same factor as before, since the experimental conditions have not changed.

We should note here the definition of the mean time $m_1$ for a distribution g(t):

$$m_1 = \int_{-\infty}^{\infty} tg(t)dt \Big/ \int_{-\infty}^{\infty} g(t)dt$$

In the notations presented above, the denominator (the time integral of g) of this expression constitutes $m_0$.

The mean time of the function $\Phi_N$ is written:

$$m_1(\Phi^N) = m_1\left(\frac{\Phi_f}{\Phi^{min}}\right)$$
$$= m_1(\Phi_f) - m_1(\Phi^{min})$$

The expression of the mean time $m_1(\Phi_f)$ is as follows:

$$m_1(\Phi_f) = \frac{1}{m_0(\Phi_f)} \sum_{v=\text{voxels}} \left\{ \begin{array}{c} \left(\frac{r_{sr_v} + r_{r_vd}}{2c\sqrt{\mu_a D}} + \tau(r_v)\right) \frac{1}{D^2} G_x(r_{sr_v}, \omega = 0) \times \\ G_m(r_{r_vd}, \omega = 0) \alpha h^3 \eta(r_v) C(r_v) \end{array} \right\} \quad (27)$$

and $m_0(\Phi_f)$ is written:

$$m_0(\Phi_f) = \sum_v \frac{1}{D^2} G_x(r_{sr_v}, \omega = 0) G_m(r_{r_vd}, \omega = 0) \alpha h^3 \eta(r_v) C(r_v) \quad (28)$$

This amount is in fact known by the measurement: $\Phi_f$ is measured, and $m_0(\Phi_f)$ (as well as $m_1(\Phi_f)$) can be deduced from this function $\Phi_f$ obtained experimentally.

The term $\tau$ is dependent on the environment of the fluorophore. However, it can be assumed that this environment is the same for the different fluorophores during a single measurement. Therefore, if the assumption is made that $\tau$ is independent of $r_v$, this term $\tau$ is removed from the sum, and it is possible to simplify the expression of $m_1(\Phi_f)$:

$$m_1(\Phi_f) = \frac{1}{m_0(\Phi)} \sum_v \left\{ \begin{array}{c} \left(\frac{r_{sr_v} + r_{r_vd}}{2c\sqrt{\mu_a D}}\right) \frac{1}{D^2} G_x(r_{sr_v}, \omega = 0) \times \\ G_m(r_{r_vd}, \omega = 0) \alpha h^3 \eta(r_v) C(r_v) \end{array} \right\} + \tau \quad (29)$$

For $m_1(\Phi^{min})$, the expression is the same by changing $\Phi$ by $\Phi_{min}$ and $r_s$ by $r_{sm}$ (respectively, rd by $r_{dm}$). Thus, in the calculation of the mean time of $\Phi^N$, the fluorescence lifetime disappears in the subtraction, and the following is obtained:

$$m_1(\Phi^N) = \frac{1}{m_0(\Phi_f)} \sum_v \left\{ \left(\frac{r_{sr_v} + r_{r_vd}}{2c\sqrt{\mu_a D}}\right) \frac{1}{D^2} G_x(r_{sr_v}, \omega = 0) G_m(r_{r_vd}, \omega = 0) \alpha h^3 \eta(r_v) C(r_v) - \right. \\ \left. \frac{1}{m_0(\Phi^{min})} \sum_v \left(\frac{r_{s_mr_v} + r_{r_vd_m}}{2c\sqrt{\mu_a D}}\right) \frac{1}{D^2} G_x(r_{s_mr_v}, \omega = 0) G_m(r_{r_vd_m}, \omega = 0) \alpha h^3 \eta(r_v) C(r_v) \right\} \quad (30)$$

We can express this quantity linearly as a function of $\alpha\eta(r_v) C(r_v)$, the quantity to be reconstructed, by adding a weight function:

$$m_1(\Phi^N) = \sum_v P^{m_0 m_1}_{(r_s, r_d), r_v} \cdot [\alpha\eta(r_v) C(r_v)]$$

with:

$$P^{m_0 m_1}_{(r_s, r_d), r_v} = \frac{1}{m_0(\Phi_f)} \left\{ \left(\frac{r_{sr_v} + r_{r_vd}}{2c\sqrt{\mu_a D}}\right) \frac{1}{D^2} G_x(r_{sr_v}, \omega = 0) G_m(r_{r_vd}, \omega = 0) h^3 \right\} - \\ \frac{1}{m_0(\Phi^{min})} \left\{ \left(\frac{r_{s_mr_v} + r_{r_vd_m}}{2c\sqrt{\mu_a D}}\right) \frac{1}{D^2} G_x(r_{s_mr_v}, \omega = 0) G_m(r_{r_vd_m}, \omega = 0) h^3 \right\}$$

Consequently, $m_1(\Phi^N)$ is measured, the ratios $$\frac{1}{m_0(\Phi_f)} \text{ and } \frac{1}{m_0(\Phi^{min})}$$

are also measured and injected into the weight function P, which is calculated, the system of linear equations is thus established, independently of the value of the fluorescence lifetime.

In other words, we return to the resolution of a system:

$$M = P \times C$$

where M is a measurement column vector, P is a weight matrix (which depends on the model chosen, therefore the function G and quantities $$\frac{1}{m_0(\Phi_f)} \text{ and } \frac{1}{m_0(\Phi^{min})}$$

and C an unknown column vector (vector proportional to the fluorophore concentrations). Once the system has been solved, the components of vector C that can be represented 3 dimensionally are known.

The solution can therefore be represented with an operator on display means such as means 27 of FIG. 1A or 1B.

The data processing means 24 make it possible to solve a system of equations such as the system above, and are therefore programmed for this purpose.

The resolution of the problem of the location or spatial distribution of fluorophores can implement one or more of the various techniques described, for example, in A. C. Kak et al. "Principles of computerized tomographic imaging", IEEE, NY, 1987.

The data can also be acquired in frequency mode at various frequencies so as to recostruct the TPSFs by performing a Fourier transform.

The developments above show that it is possible to use, in the context of the invention, a function of the frequency. This frequency function can be normalised, for example with respect to the frequency function that corresponds to the minimum mean time.

The invention claimed is:

1. Method for processing fluorescence signals emitted, after excitation by radiation from a radiation source, by at least one fluorophore with a lifetime $\tau$ in a surrounding medium, which signals are detected by detection means, which method comprising:

detecting, for each pair of positions of the radiation source and the detection means, a fluorescence signal $\Phi_{fluo}$ emitted by said at least one fluorophore in its surrounding medium via a detector;

calculating, based on the detected fluorescence signals, values of a variable, independent of the lifetime $\tau$ using a computer; and determining a position or a spatial distribution and/or a concentration of said at least one fluorophore in said medium on the basis of the values of said variable using the computer.

2. Method according to claim 1, wherein said variable is independent of $\tau$ resulting from a frequency normalised function.

3. Method according to claim 2, wherein said function being frequency normalised with respect to a specific fluorescence signal.

4. Method according to claim 3, wherein said specific fluorescence signal has a minimum mean time or a minimum calculated mean time.

5. Method according to claim 1, wherein said variable is independent of $\tau$ resulting from a difference between a first mean time calculated for each fluorescence signal and a second mean time calculated for a specific fluorescence signal.

6. Method according to claim 5, wherein said specific fluorescence signal has a minimum mean time or a minimum calculated mean time.

7. Method according to claim 1, wherein said variable is calculated from Mellin-Laplace transforms on the basis of fluorescence signals or moments of orders greater than the normalised fluorescence functions.

8. Method according to claim 1, wherein the position or the spatial distribution of said at least one fluorophore in said medium is determined by a method of reversal technique using values of said variable.

9. Method according to claim 8, wherein the position or the spatial distribution is determined using a minimisation of an error function using a simplex function.

10. Method according to claim 1, wherein the position or the spatial distribution of said at least one fluorophore in said medium is determined by implementing a system of linear equations comprising:

$M = P \times C$, where M is a measurement column vector, P is a weight matrix and C is a distribution column vector.

11. Method according to claim 1, further comprising calculating a first moment of a fluorescence curve of the fluorescence signals as a function of time.

12. Method according to claim 1, further comprising displaying a visual or graphic representation of the position or the spatial distribution of the at least one fluorophore.

13. Method according to claim 1, wherein the radiation is of a femtosecond type.

14. Method according to claim 1, wherein the fluorescence signals are detected by a TCSPC technique or by camera.

15. Method according to claim 1, further comprising measuring the fluorescence signals by the surrounding medium, in absence of a fluorophore; and correcting the fluorescence signals $\Phi_{fluo}$ emitted by the fluorophore in the surrounding medium.

16. Device for processing fluorescence signals emitted by at least one fluorophore, with a lifetime $\tau$ in a surrounding medium, comprising:

a source of radiation for excitation of said at least one fluorophore, means for detecting a fluorescence signal emitted by said fluorophore, wherein the source and the detection means are moveable relative to said at least one fluorophore;

means for calculating values of a variable independent of $\tau$, on the basis of a plurality of fluorescence signals $\Phi_{fluo}$ emitted by the fluorophore into its surrounding medium, with each signal corresponding to a relative position of the fluorophore and the source and the detection means to determine a position or a spatial distribution and/or a concentration of said at least one fluorophore in said medium based on the calculated values of said variable.

17. Device according to claim 16, wherein said detection means comprising a TCSPC-type means or a camera-type means.

18. Device according to claim 16, further comprising means for visual or graphic representation of the position or the spatial distribution of the at least one fluorophore.

19. Device according to claim 16, wherein said variable is independent of $\tau$ resulting from a normalised frequency function.

20. Device according to claim 19, wherein said function is frequency normalized with respect to a specific fluorescence signal.

21. Device according to claim 20, wherein said specific fluorescence signal has a minimum mean time or a minimum calculated mean time.

22. Device according to claim 16, wherein said variable is independent of $\tau$ resulting from a difference between a mean time $\tau$ calculated for each fluorescence signal and a mean time calculated for a specific fluorescence signal.

23. Device according to claim 22, wherein said specific fluorescence signal has a minimum mean time or a minimum calculated mean time.

24. Device according to claim 16, wherein said variable is calculated from Mellin-Laplace transforms of the fluorescence signals or moments of greater orders of normalised fluorescence functions.

25. Device according to claim 16, wherein said means for determining the position or the spatial distribution of said at least one fluorophore in said medium implements a method of reversal technique using values of said variable.

26. Device according to claim 16, wherein statistical processing of the values of said variable being a minimisation of an error function using a simplex method.

* * * * *